(12) United States Patent
Maschmeyer

(10) Patent No.: US 8,889,935 B2
(45) Date of Patent: Nov. 18, 2014

(54) PROCESS FOR PREPARING 1-BUTENE AND A 1,3-BUTADIENE DERIVATIVE

(75) Inventor: Dietrich Maschmeyer, Recklinghausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/009,722

(22) PCT Filed: Mar. 21, 2012

(86) PCT No.: PCT/EP2012/054975
§ 371 (c)(1),
(2), (4) Date: Dec. 16, 2013

(87) PCT Pub. No.: WO2012/136479
PCT Pub. Date: Oct. 11, 2012

(65) Prior Publication Data
US 2014/0114094 A1    Apr. 24, 2014

(30) Foreign Application Priority Data

Apr. 4, 2011 (DE) .......................... 10 2011 006 721

(51) Int. Cl.
| | |
|---|---|
| C07C 5/327 | (2006.01) |
| C07C 5/05 | (2006.01) |
| C07C 43/15 | (2006.01) |
| C07C 2/06 | (2006.01) |
| C07C 5/333 | (2006.01) |
| C07C 7/163 | (2006.01) |
| C07C 7/04 | (2006.01) |

(52) U.S. Cl.
CPC . *C07C 5/327* (2013.01); *C07C 2/06* (2013.01); *C07C 5/05* (2013.01); *C07C 7/163* (2013.01); *C07C 5/333* (2013.01); *C07C 43/15* (2013.01); *C07C 7/04* (2013.01)
USPC .............................. 585/254; 585/251; 585/379

(58) Field of Classification Search
None
See application file for complete search history.

(56) References Cited

U.S. PATENT DOCUMENTS

| | | | |
|---|---|---|---|
| 7,115,790 B2 | 10/2006 | Beller et al. | |
| 7,342,144 B2 | 3/2008 | Kaizik et al. | |
| 7,354,883 B2 | 4/2008 | Kaizik et al. | |
| 7,371,909 B2 | 5/2008 | Beller et al. | |
| 7,462,745 B2 | 12/2008 | Nierlich et al. | |
| 2007/0055088 A1* | 3/2007 | Schindler et al. | ............. 585/702 |
| 2007/0161841 A1 | 7/2007 | Schindler et al. | |
| 2007/0167661 A1 | 7/2007 | Johann et al. | |
| 2013/0172641 A1 | 7/2013 | Boeing et al. | |

FOREIGN PATENT DOCUMENTS

| | | |
|---|---|---|
| DE | 102 31 633 A1 | 1/2004 |
| DE | 103 50 045 A1 | 5/2005 |
| WO | WO 2005/063658 A1 | 7/2005 |

OTHER PUBLICATIONS

International Search Report issued Sep. 7, 2013 in Application No. PCT/EP2012/054975.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

A process for preparing 1-butene and a 1,3-butadiene derivative, containing the steps of a) non-oxidatively catalytically dehydrogenating a feedstock gas stream containing n-butane, hydrogen, other low-boiling secondary constituents and high boilers, to form a product mixture containing unreacted n-butane, 1-butene, 2-butenes, 1,3-butadiene, hydrogen, other low-boiling secondary constituents and high boilers; b) removing hydrogen, other low boilers and high boilers, to give a product mixture containing n-butane, 1-butene, two 2-butenes and 1,3-butadiene; c) reacting some of the 1,3-butadiene obtained in the removing b), to form a derivative; d) removing the 1,3-butadiene derivative obtained in the reacting c); e) selectively hydrogenating the 1,3-butadiene not derivatized in the reacting c), to form 1-butene; and f) distillatively removing 1-butene from the hydrocarbon stream obtained in the hydrogenating e), to leave a residual stream.

14 Claims, 2 Drawing Sheets

PROCESS FOR PREPARING 1-BUTENE AND A 1,3-BUTADIENE DERIVATIVE

The present invention relates to a process for preparing 1-butene and a 1,3-butadiene derivative from n-butane or a mixture of linear $C_4$ hydrocarbons containing n-butane.

1-Butene and derivatives of 1,3-butadiene are important intermediates in the production of a multiplicity of products. For example, 1-butene can be used for modifying ethylene or propylene polymers. The downstream butadiene product 1-methoxy-2,7-octadiene, for example, is an intermediate in the synthesis of 1-octene.

Unsaturated $C_4$ hydrocarbons can be recovered from the $C_4$ fractions from crackers, such as steam crackers or FC crackers, for example, that are operated for producing propylene and ethylene. For example, 1-butene and 1,3-butadiene can be removed from the $C_4$ fraction from a steam cracker, and 1-butene from the $C_4$ cut from an FC cracker. The amounts of $C_4$ cuts are tied to the production of ethylene and propylene, and are not available to a sufficient extent.

As an alternative, linear unsaturated $C_4$ hydrocarbons can be prepared by dehydrogenation of n-butane. This produces a reaction mixture comprising unreacted n-butane, 1-butene, the two 2-butenes and 1,3-butadiene.

DE 103 50 045 describes a process for recovering 1-butene from n-butane. This method involves dehydrogenating n-butane and, following removal from the dehydrogenation product of those by-products that are not $C_4$ hydrocarbons, selectively hydrogenating the butadiene to form linear butenes. 1-Butene is removed distillatively from the hydrogenation mixture, and the remaining mixture, consisting primarily of 2-butenes and n-butane, is recycled to the dehydrogenation stage.

DE 102 31 633 discloses a process for preparing 4-vinylcyclohexene from n-butane. This process involves dehydrogenating n-butane and, following removal from the dehydrogenation product of those by-products that are not $C_4$ hydrocarbons, catalytically reacting the butadiene to form 4-vinylcyclohexene. Following removal of the 4-vinylcyclohexene, the remaining hydrocarbon mixture, comprising the linear butenes, n-butane and possibly butadiene, is returned to the dehydrogenation reactor.

What these two processes have in common is that in each case only one component is recovered from the dehydrogenation mixture.

Besides the linear butenes, the reaction mixture obtained in the dehydrogenation of n-butane comprises n-butane and 1,3-butadiene. The recovery of pure 1-butene and pure 1,3-butadiene, the latter being amenable to reaction in further step to give downstream products, from mixtures of this kind by distillation is uneconomic, owing to the small differences between them in boiling point. Similarly, the removal of the 1,3-butadiene by extraction or extractive distillation is complex and expensive.

The object of the present invention is to provide a process which allows 1-butene and a butadiene derivative to be prepared economically from n-butane.

This object is achieved by means of the process described hereinafter.

A process for preparing 1-butene and a 1,3-butadiene derivative, comprising the steps of:
a) non-oxidatively catalytically dehydrogenating a feedstock gas stream comprising n-butane, hydrogen, other low-boiling secondary constituents, high boilers and optionally water, to form a product mixture comprising unreacted n-butane, 1-butene, the two 2-butenes, 1,3-butadiene, hydrogen, other low-boiling secondary constituents, high boilers and optionally water, the feedstock gas stream containing no $C_4$ iso compounds;
b) removing hydrogen, other low boilers, high boilers and, if present, water, to give a product mixture comprising n-butane, 1-butene, the two butenes and 1,3-butadiene;
c) reacting some of the 1,3-butadiene obtained in step b), to form a derivative;
d) removing the 1,3-butadiene derivative obtained in step c);
e) selectively hydrogenating the 1,3-butadiene not derivatized in step c), to form 1-butene;
f) distillatively removing 1-butene from the hydrocarbon stream obtained in step e), to leave a residual stream.

In one embodiment of the process, the residual stream obtained in step f) is supplied wholly or partly to the feedstock gas stream, in other words back into the dehydrogenating unit in which step a) of the process takes place.

The present invention has the advantage that 1-butene and a butadiene derivative can be prepared inexpensively from n-butane. The proportion of the two target products here can be varied by adjusting the dehydrogenating conditions and the butadiene conversion rate. The specific version of the invention is notable, furthermore, for the fact that a very high fraction of the olefins formed during the dehydrogenation are converted into valuable products, and so only a small amount of butenes is introduced with the recycle stream into the dehydrogenation reactor.

In one embodiment of the invention, the linear butenes present in the residual stream are at least partly reacted prior to the supplying, and the reaction products are removed from the residual stream prior to the supplying.

In one embodiment of the invention, this reaction is an oligomerization.

FEEDSTOCKS

Figure 1:
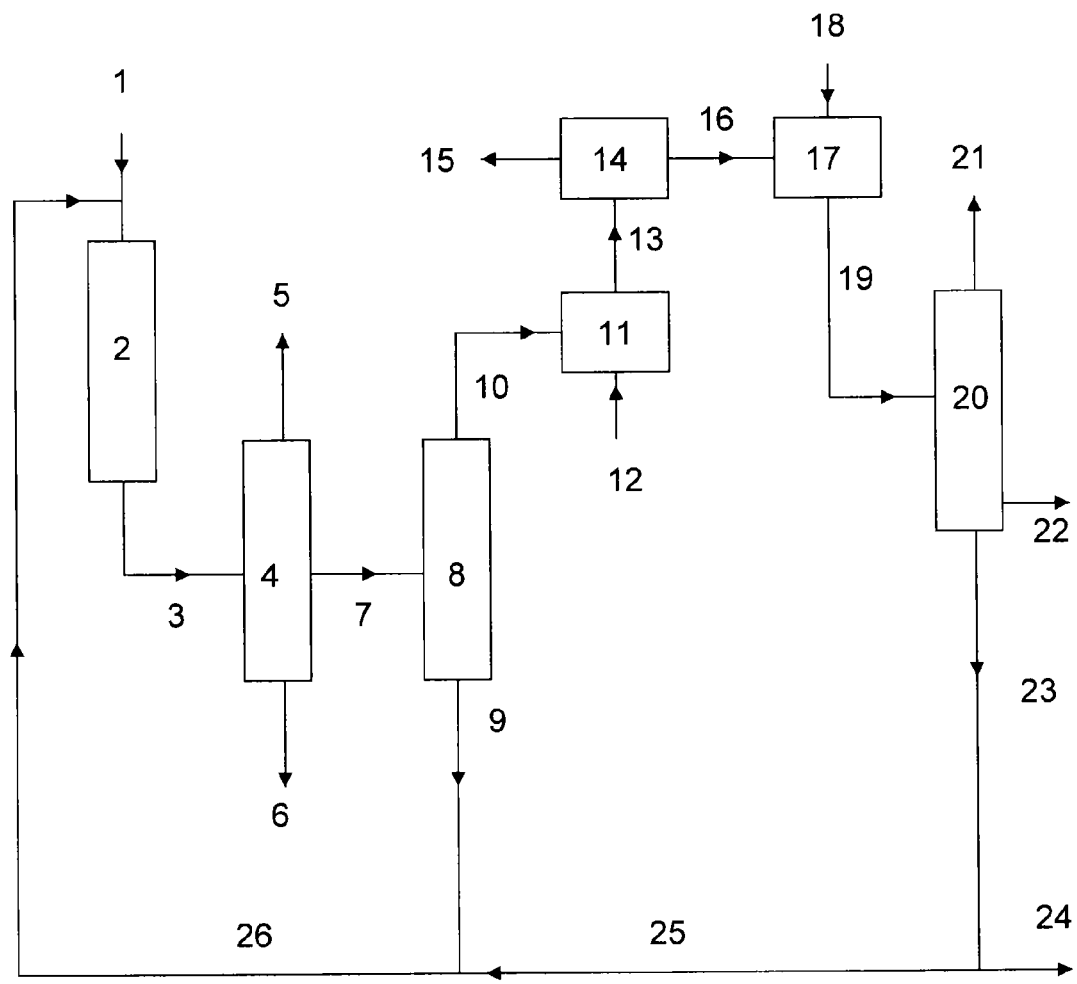
FIG. 1 is a working example of the feedstock stream of the present invention.

Feedstocks which can be used for the process of the invention include the n-butane fraction from field butanes, mixtures of linear $C_4$ hydrocarbons produced in the processing of $C_4$ cuts from steam crackers or FC crackers, or other mixtures of linear $C_4$ hydrocarbons that are produced in other industrial operations.

Field butanes is the term used for the $C_4$ fraction of the "wet" fractions of natural gas and also of the gases accompanying petroleum, said fractions being removed in liquid form from the gases by cooling to around −30° C. Low-temperature distillation produces the field butanes, their composition varying according to deposit, but generally containing about 30% by mass of isobutane and 65% by mass of n-butane. Other constituents are generally about 2% by mass of hydrocarbons with fewer than 4 C atoms, and about 3% by mass of hydrocarbons with more than 4 C atoms. Following distillative removal of the isobutane, this mixture can be used in the process of the invention. As an option, before the dehydrogenating step in the process of the invention, the hydrocarbons that do not have 4 C atoms can be removed wholly or partly as well.

In one embodiment of the process, the feedstock gas stream from step a) is the n-butane fraction from field butanes.

In another embodiment of the process, the feedstock gas stream from step a) is a mixture of linear $C_4$ hydrocarbons from the processing of $C_4$ cuts from steam crackers or FC crackers.

Derivatization of 1,3-Butadiene

The hydrocarbon mixture obtained following removal of the by-products comprises essentially n-butane, 1-butene, the two 2-butenes and 1,3-butadiene.

This mixture is subjected to a reaction in which the 1,3-butadiene, but not the linear butenes, is reacted.

In one embodiment of the process, 1,3-butadiene is reacted in step c) to form a derivative selected from the following: 4-vinylcyclohexene, 1,4-cyclooctadiene, 1,5,9-cyclododecatriene, 4-cyclohexene-1,2-dicarboxylic acid derivatives, 1,7-octadiene, unbranched acyclic octatrienes, 2,7-octadienyl derivatives.

The reaction of 1,3-butadiene to 4-vinylcyclohexene may take place, for example, over supported Cu(I) catalysts, such as in U.S. Pat. No. 5,196,621 or according to EP 0 397 266.

1,3-Butadiene can be reacted in the presence of dissolved nickel-organoaluminium catalysts to form 1,4-cyclooctadiene and/or 1,5,9-cyclododecatriene.

The reductive dimerization of 1,3-butadiene to form 1,7-octadiene can be carried out in accordance with DE 101 49 347 or DE 10 2006 031413.1.

The dimerization of 1,3-butadiene to form octatriene, more particularly 1,3,7-octatriene, can be carried out over a palladium carbene complex, as described in DE 10 2004 060520.

In one embodiment of the process, the 1,3-butadiene is reacted in step c) with dienophiles which have an electron-deficient C—C multiple bond, to form Diels-Alder products. The multiple bond may be a C—C double bond or a C—C triple bond.

Examples of dienophiles with triple bonds are as follows: Propynoic acid; propynoic esters, where the radical attached to the oxygen atom of the ester may have 1 to 20 C atoms; propynal; propynol; acetylenedicarboxylic acid; acetylenedicarboxylic monoesters and acetylenedicarboxylic diesters, in which the radical or radicals attached to an oxygen atom of the ester may have 1 to 20 C atoms; 3-formylpropynoic acid and its esters; butynedial; butynediol.

Dienophiles having double bonds have at least one double bond which is conjugated and substituted by one or more electron-withdrawing group(s). Corresponding electron-withdrawing groups (-M effect) are as follows: nitro group, cyano group, formyl radical, keto radical (—C(O)R), acid radical (—C(O)OH), ester radical (—C(O)OR) or anhydride radical (—C(O)OC(O)R).

It is also possible for two vincial substituents together to form a functional group, such as an anhydride group, for example.

Dienophiles used with preference are as follows:

Maleic anhydride; maleic acid and its alkyl esters in which the alkyl radicals may be identical or different and each have 1 to 10 C atoms, more particularly 1 to 4 C atoms; fumaric acid and its alkyl esters in which the alkyl radicals may be identical or different and each have 1 to 10 C atoms, more particularly 1 to 4 C atoms; maleimide (maleic imide) and its N-substituted derivatives in which the substituent on the nitrogen has 1 to 10, more particularly 1 to 4, C atoms.

This produces derivatives of 4-cyclohexene-1,2-dicarboxylic acid. These derivatives may be converted into esters of 1,2-cyclohexanedicarboxylic acid by, for example, hydrogenation of the double bond and subsequent alcoholysis (esterification, transesterification). These esters with ester alkyl groups containing 7 to 12 C atoms are used as plasticizers, an example being diisononyl 1,2-cyclohexanedicarboxylate.

In one embodiment of the process, 1,3-butadiene is reacted with a protic nucleophile (water, alcohols, amines) to form the corresponding 2,7-octadienyl derivative, the nucleophile radical being attached to the C1. This reaction (telomerization) is catalysed by palladium complexes. It is preferred to use palladium carbene complexes, as described in DE 101 28 144 and DE 103 12 829, for example.

The telomerization may be carried out similarly to the manner described in DE 10 2005 036039, with the difference that there is no need for preliminary hydrogenative purification of the feedstock stream.

In one embodiment of the process the 2,7-octadienyl derivative formed is 1-methoxyocta-2,7-diene.

1-Methoxyocta-2,7-diene is a prized telomerization product. It can be used, by hydrogenation of the two olefinic double bonds and subsequent methanol elimination, to obtain 1-octene, which is used industrially for modifying polyethylene or polypropylene. The three-stage synthesis for 1-octene starting from 1,3-butadiene is published in DE 101 49 348, for example. For the elimination of methanol from 1-methoxyoctane, it is possible to use the catalyst claimed in DE 102 57 499.

Selective Hydrogenation

The $C_4$ hydrocarbon mixture that remains following removal of the butadiene derivative comprises not only unreacted 1,3-butadiene but also 1-butene and, if they have not already been removed beforehand, n-butane and the two 2-butenes. The remainders of 1,3-butadiene and any polyunsaturated hydrocarbons present, such as 1,2-butadiene, for example, are removed by selective hydrogenation, which also increases the fractions of n-butenes. One suitable process is that described, for example, by F. Nierlich et al. in Erdöl & Kohle, Erdgas, Petrochemie, 1986, page 73 ff. It operates in liquid phase with fully dissolved hydrogen in stoichiometric amounts. Examples of suitable selective hydrogenation catalysts include nickel and especially palladium on a support, such as 0.3% by mass of palladium on activated carbon or aluminium oxide, for example. A small amount of carbon monoxide, in the ppm range, promotes the selectivity of the hydrogenation of 1,3-butadiene to the linear butenes, and counteracts the formation of polymers, referred to as "green oil", that deactivate the catalyst.

Removal of 1-Butene

The hydrogenation discharge is separated by distillation into 1-butene and a mixture of n-butane and linear butenes, primarily 2-butenes.

Use of Distillate Fractions

The 1-butene recovered contains no iso compounds. It can be used in particular for the preparation of cooligomers with ethylene or propylene, or as a comonomer in polyolefins (LLDPE).

In another embodiment of the process, the 1-butene recovered in step f) is reacted in a subsequent step g) to form cooligomers with ethylene or propylene.

The n-butane/2-butene fraction can be returned wholly or partly to the dehydrogenation reactor.

Prior to the recycling, optionally, a portion of the linear butenes can be removed by reaction and removal of the reaction products.

Suitable reactions which yield prized intermediates are, for example, oligomerization or hydroformylation.

The oligomerization can be carried out using acidic or nickel-containing catalysts, homogeneously or heterogeneously. The oligomerization takes place preferably over fixed-bed nickel catalysts. One such process, for example, is the Octol process of Evonik Oxeno GmbH. The olefins formed primarily in that process, with 8 and 12 C atoms, are intermediates in the preparation of plasticizers or detergents.

In the case of the hydroformylation, a mixture of n-pentanal and 2-methylbutanal is formed. Through the choice of catalyst used it is possible to vary the proportion of the two aldehydes by mass. Under isomerizing conditions it is possible to prepare n-pentanal in a selectivity of more than 95%. This can be done using a catalyst system such as that described in EP 0 213 639, for example. Such mixtures are especially suitable for the preparation of decanol mixtures with a high fraction of 2-propylheptanol.

WORKING EXAMPLE

Figure 2:
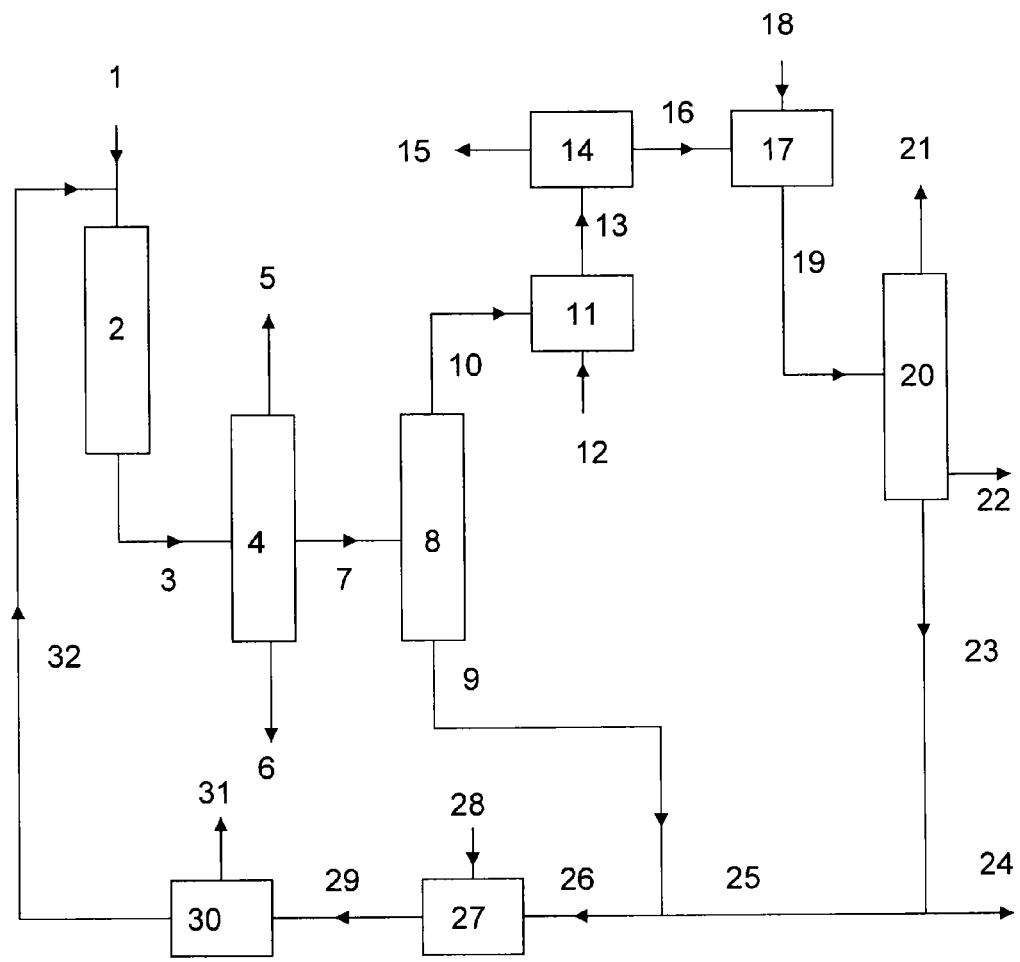
FIG. 2 is another working example of the feedstock stream of the present invention.

Two working examples of the present invention are elucidated by means of the block diagrams in FIGS. 1 and 2.

The working example illustrated in FIG. 1 sees the feedstock stream (1) containing n-butane being introduced together with the recycled stream (25/26) into the dehydrogenating unit (2) (optionally, steam or oxygen can be introduced; this is not shown in FIG. 1). The dehydrogenation mixture (3) is separated in a distillation unit (4) into low boilers (5), high boilers, including water (6), and a $C_4$ fraction (7). From stream (7), a part of the n-butane and of the two 2-butenes is removed stream (9), which is returned to the dehydrogenation reactor. A portion of the 1,3-butadiene in the overhead stream (10) is derivatized in the reactor (11), optionally with addition of an agent (12). Removed from the reaction mixture (13) in the processing apparatus (14) are the butadiene derivative (15), a target product, and the $C_4$ fraction (16). The removal of any agent present, and of catalyst, and the return of these components, is not shown. The C4 stream (16), which still contains small amounts of 1,3-butadiene, is selectively hydrogenated in the reactor (17) with hydrogen (18). The hydrogenation discharge (19) is separated in the hydrogenating unit (20) into 1-butene (21), second target product (22), into a mixture (23) of n-butane and linear butenes, and optionally a fraction containing high boilers. Optionally after removal of a sub-stream (24), the stream (23) is returned to the dehydrogenation reactor.

In this embodiment, the column (8) is optional. Using the column provides the advantage that the concentration of 1,3-butadiene in the stream (10) is increased. As a result, a higher conversion rate for 1,3-butadiene can be achieved in the reactor (11). A disadvantage, however, are the capital costs and operating costs involved in the column.

A second embodiment to the present invention is set out in FIG. 2. It differs from embodiment 1 in that from the recycled stream (26) a portion of the linear butenes is reacted in the reactor (27), optionally with addition of an agent (28), to form the stream (29), consisting of n-butane, unreacted butenes and the product of the reaction. Following removal of the reaction products (31) and optionally of other substances in the separating apparatus (30), stream (32), which comprises n-butane and linear butenes, is fed into the dehydrogenation reactor.

With this embodiment it is optional to feed only stream (9) or only stream (23), or portions of these two streams in any desired ratio, into the reactor.

The invention claimed is:

1. A process for preparing 1-butene and a 1,3-butadiene derivative, comprising:
    a) non-oxidatively catalytically dehydrogenating a feedstock gas stream comprising n-butane, hydrogen, other low-boiling secondary constituents and high boilers, to form a product mixture comprising unreacted n-butane, 1-butene, two 2-butenes, 1,3-butadiene, hydrogen, other low-boiling secondary constituents and high boilers;
    b) removing hydrogen, other low boilers and high boilers, to give a product mixture comprising n-butane, 1-butene, two 2-butenes and 1,3-butadiene;
    c) reacting some of the 1,3-butadiene obtained in the removing b), to form a derivative;
    d) removing the 1,3-butadiene derivative obtained in the reacting c);
    e) selectively hydrogenating the 1,3-butadiene not derivatized in the reacting c), to form 1-butene; and
    f) distillatively removing 1-butene from the hydrocarbon stream obtained in the hydrogenating e), to leave a residual stream.

2. The process according to claim 1, wherein the residual stream obtained in the distillatively removing f) is supplied wholly or partly to the feedstock gas stream.

3. The process according to claim 2, wherein the 2-butenes present in the residual stream are at least partly reacted before the supplying, and reaction products are removed from the residual stream before the supplying.

4. The process according to claim 3, wherein the reaction is an oligomerization.

5. The process according to claim 1, wherein the feedstock gas stream from the dehydrogenating a) is an n-butane fraction of field butanes.

6. The process according to claim 1, wherein the feedstock gas stream from the dehydrogenating a) is a mixture of linear $C_4$ hydrocarbons from processing of $C_4$ cuts from steam crackers or FC crackers.

7. The process according to claim 1, wherein the reacting c) of 1,3-butadiene forms a derivative selected from the group consisting of 4-vinylcyclohexene, 1,4-cyclooctadiene, 1,5,9-cyclododecatriene, 4-cyclohexene-1,2-dicarboxylic acid derivative, 1,7-octadiene, unbranched acyclic octatriene, and 2,7-octadienyl compound.

8. The process according to claim 1, wherein the 1,3-butadiene is reacted in the reacting c) with dienophiles which have an electron-deficient C—C multiple bond, to form a Diels-Alder product.

9. The process according to claim 8, wherein the dienophile is selected from the group consisting of:
    maleic anhydride,
    maleic acid and its alkyl ester in which the alkyl radicals may be identical or different and each have 1 to 10 C atoms,
    fumaric acid and its alkyl ester in which the alkyl radicals may be identical or different and each have 1 to 10 C atoms, and
    maleimide and its N-substituted derivative in which a substituent on the nitrogen has 1 to 10 C atoms.

10. The process according to claim 1, wherein the 1,3-butadiene is reacted in the reacting c) with a protic nucleophile to form a corresponding 2,7-octadienyl derivative, and a nucleophile residue is attached to C1.

11. The process according to claim 10, wherein the 2,7-octadienyl compound formed is 1-methoxyocta-2,7-diene.

12. The process according to claim 1, wherein the selective hydrogenating e) takes place in the presence of a palladium catalyst.

13. The process according to claim 12, wherein the palladium catalyst is applied on a support selected from the group consisting of activated carbon and aluminium oxide.

14. The process according to claim 1, wherein the 1-butene recovered in the removing f) is subsequently reacted to form cooligomers with ethylene or propylene.

* * * * *